United States Patent [19]

Tagaya et al.

[11] Patent Number: 4,615,622

[45] Date of Patent: Oct. 7, 1986

[54] PROCESS FOR DETECTING RESIDENT AIR IN A LIQUID CHARGED RECEPTACLE AND APPARATUS THEREFOR

[75] Inventors: Ryosaku Tagaya, Isesaki; Osamu Kojima, Fujioka; Yasuo Sonobe, Misato, all of Japan

[73] Assignee: Eisai Co., Ltd., Tokyo, Japan

[21] Appl. No.: 621,262

[22] Filed: Jun. 15, 1984

[30] Foreign Application Priority Data

Jun. 24, 1983 [JP]  Japan .................................. 58-113823

[51] Int. Cl.⁴ ............................................ G01N 21/90
[52] U.S. Cl. ................................ 356/427; 250/223 B; 356/240; 356/244
[58] Field of Search ....................... 356/240, 426–428, 356/445–448, 244; 250/223 B

[56] References Cited

U.S. PATENT DOCUMENTS

| | | | |
|---|---|---|---|
| 3,811,567 | 5/1974 | Tomita et al. | 356/427 X |
| 3,900,266 | 8/1975 | Takahashi et al. | 356/427 X |
| 4,241,256 | 12/1980 | Tagaya et al. | 356/240 X |

Primary Examiner—Vincent P. McGraw
Assistant Examiner—Robert D. V. Thompson, III
Attorney, Agent, or Firm—Murray and Whisenhunt

[57] ABSTRACT

A perspective receptacle charged with liquid and having its mouth portion sealed with an opaque seal member is rotated as-erected at a high speed. Due to this high speed rotation, the air resident in the vicinity of the mouth portion of the receptacle forms an air cavity and descends below the seal member. This descending air cavity is detected from the outside of the receptacle by means of an optical detecting member.

6 Claims, 8 Drawing Figures

PROCESS FOR DETECTING RESIDENT AIR IN A LIQUID CHARGED RECEPTACLE AND APPARATUS THEREFOR

BACKGROUND OF THE INVENTION

This invention relates to a process for easily detecting an air resident in a liquid-charged transparent receptacle, especially the air that floats above the liquid contained in the receptacle and is difficult to detect it by the eye from the outside because the view of air is interrupted by an opaque seal member attached to the mouth portion of the receptacle.

Recently, in the fields of medical treatment, for instance dental treatment and the like there is being used a receptacle which comprises charging the transparent receptacle 1 shown in FIG. 1A and FIG. 1B with an anesthetic or the like, plugging its bottom portion with a rubber plug 2 which is also usable as pistons, covering a mouth portion with a rubber film 3, and sealing it with an opaque seal member 4 such as an aluminum foil. In the practical use of this receptacle, a rear end of an injection needle (not shown) is injected in the rubber film 3, the rubber plug 2 is used as a piston, and consequently the receptacle 1 itself is used in the same manner as the usual injector. Accordingly, upon charging the liquid, it is not permitted to use a receptacle containing the air over the prescribed amount. Such receptacles must be abolished as inferior goods. This resident air, as shown in FIG. 1A, forms an air cavity 5 on the top portion of the liquid at the mouth portion of the receptacle and resides therein. However, as it is difficult to detect it by the eye from the outside because its view is obstructed by the seal member 4, in order to detect the air workers have made it a rule to hold it upside down, give it a shock for transferring the air toward the rubber plug 2 located upward, and detecting the air by the eye.

However, the detecting process like this, as is apparent from the aforegoing, was defective in that its operation is very complicated, it is extremely inefficient, and further a fixed accuracy can not be obtained.

SUMMARY OF THE INVENTION

It is an object of this invention to provide a detecting process which is capable of eliminating the drawbacks inherent in the aforesaid conventional detecting processes and allowing the workers to detect the resident air by the eye extremely efficiently and accurately without necessity of any operations complicated to the workers.

The inventor of this invention has carried out various studies as to whether there is a process which is capable of achieving the aforesaid object or not to find that when the amount of the air resident at the top portion is relatively much, there is formed an air cavity 5', which has a paraboloid of revolution and a lower end extending lower than the seal member as shown in FIG. 2A, by erecting the receptacle 1 and revolving it at high speed; while when the amount of said air is relatively small, there is formed a bubble-shaped air cavity 5", which subsides below the seal member 4 as shown in FIG. 2B, by stopping suddenly the receptacle 1 under high speed revolution, whereby these air cavities 5' and 5" can be detected from the outside of the receptacle. The above mentioned object can be achieved because the resident air can be indirectly detected from the detection of such air cavities by an optical detecting member.

It is another object of this invention to provide an air detecting apparatus which is capable of effect the aforesaid detecting apparatus automatically and efficiently, that is, by carrying out the high speed revolution of the receptacle and detection of air cavities mechanically without relying on a man power.

The above mentioned object can be achieved by providing an air detecting apparatus according to the present invention which comprises a receptacle holding member which holds a liquid receptacle as-erected; a supporting member which supports this receptacle holding member rotatably; a driving member which rotates said receptacle holding member at a high speed; and an optical detecting member including a projector and a ray receiver which are disposed adjacent to and below a receptacle seal member and have optical axes intersecting at the same level forming a fixed angle in the receptacle. The "high speed rotation" referred to herein denotes about 5000–6000 r.p.m. higher than 3000 r.p.m. employed at the time of detecting foreign matters. That is, the liquid receptacle rotating at high speed, depending on the amounts of the resident air at the top of the receptacle, forms the air cavity having a paraboloid of revolution during rotation or forms the bubble-shaped air cavity after the rotation is stopped. In the former the lower end of the air cavity is located lower than the seal member and in the latter the air cavity as a whole is located lower than the seal member. The light projected on said air cavities is reflected from the air cavity walls and is received by the ray receiver. Thus, the presence of resident air and the degree of resident air amounts can be detected.

In the preferred embodiment of this invention, the receptacle holding member includes a rotary pad which presses the top portion of the receptacle downward, a rotary disc which is disposed under said rotary pad and supports the bottom of the receptacle and a friction roller which is disposed co-axially with said rotary pad and is connected with the rotary disc, while the driving member includes a driving motor and a belt which is moved by said driving motor and friction contacts with said friction roller.

DETAILED DESCRIPTION OF THE INVENTION

Figure 3:
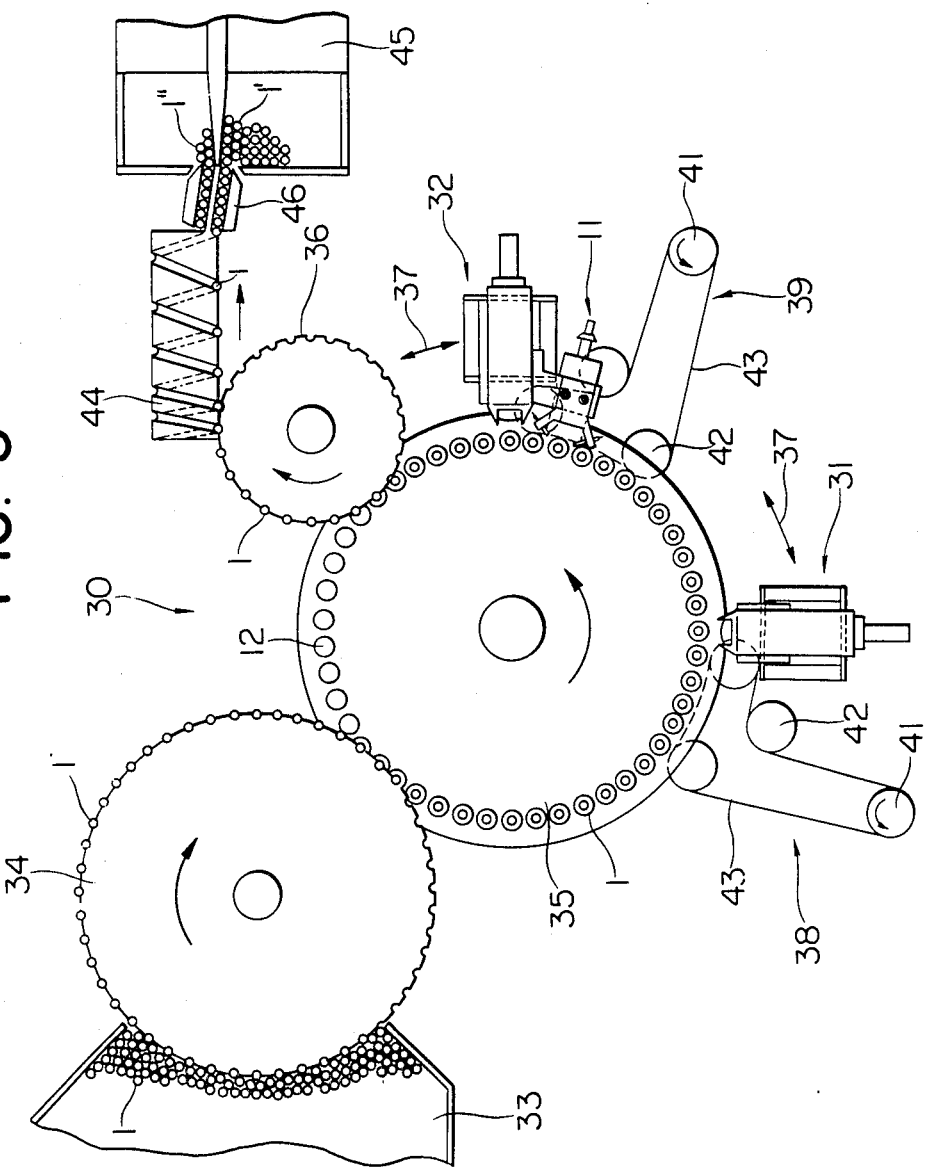
FIG. 3 is a schematic plan view illustrating an apparatus for detecting inferior goods which comprises arranging an air detecting apparatus according to this invention together with another apparatus for detecting foreign goods.

FIG. 3 schematically illustrates an apparatus for detecting inferior goods which comprises arranging an air detecting apparatus 11 according to this invention together with different first and second apparatuses 31 and 32 for detecting foreign goods. As said apparatus, from which the air detecting apparatus 11 was removed, has been disclosed in Japanese Patent Application No. 91193/1977 (now Japanese Laid Open Patent Application No. 25891/1979) filed July 29, 1977 by the assignee of this invention which is compared as reference, it is well known in the prior art and forms no part of the present invention in view of this, it will be explained here schematically.

In FIG. 3, reference numeral 33 denotes a supply hopper, and there are provided a first turntable 34 arranged to border on its supply port and rotate continuously at a fixed speed, a second turntable 35 disposed adjacent to this table 34 and designed to rotate simultaneously therewith, and a third turntable 36 disposed adjacent to this table 35 and arranged to rotate simultaneously therewith.

Figure 6:
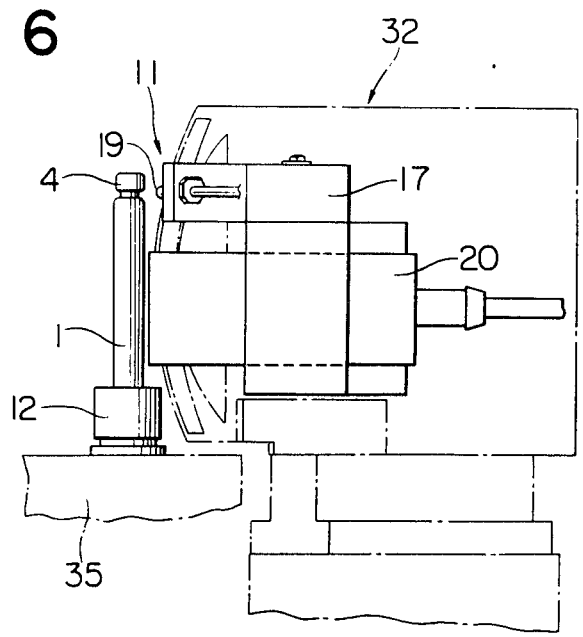
FIG. 6 is a right side view of FIG. 5.

On the circumference of the turntable 35 there are provided a first detecting apparatus 31 and a second detecting apparatus 32 so as to make a reciprocating motion in the circular direction shown by the arrow mark 37. On this side of each of these apparatuses 31 and 32 there is provided a first driving apparatus 38 and a second driving apparatus 39 respectively. These driving apparatuses 38 and 39 are same in construction and each includes a driving pulley 41 rotated by a motor 40 which is illustrated in FIG. 6 alone, plural driven pulleys 42 and a belt 43 hanged around these pulleys.

Reference numeral 44 denotes a screw conveyor for discharge and 45 denotes a conveyor for discharge respectively. Between both conveyors, there is provided a selecting member 46 oscillating vertically in FIG. 3.

The receptacle 1 is transferred from the hopper successively through turntables 34, 35 and 36, and is discharged on a conveyor 45 via a conveyor 44 from the turntable 36. During this transfer, the presence of foreign matters contained in the receptacle is detected by using the first detecting apparatus 31 and the second detecting apparatus 32 according to the method as disclosed in said reference, and in case foreign matters are detected, a signal of detection is given to the selecting member 46. Upon receiving said signal, the selecting member 46 oscillates downward in FIG. 3 so as to discharge said receptacle 1 containing foreign matters on the conveyor 45 as an inferior good 1″. In case the receptacle 1 is regarded as being superior, on the other hand, the selecting member oscillates upward so as to discharge said receptacle 1 as a superior good 1′.

Figure 4:
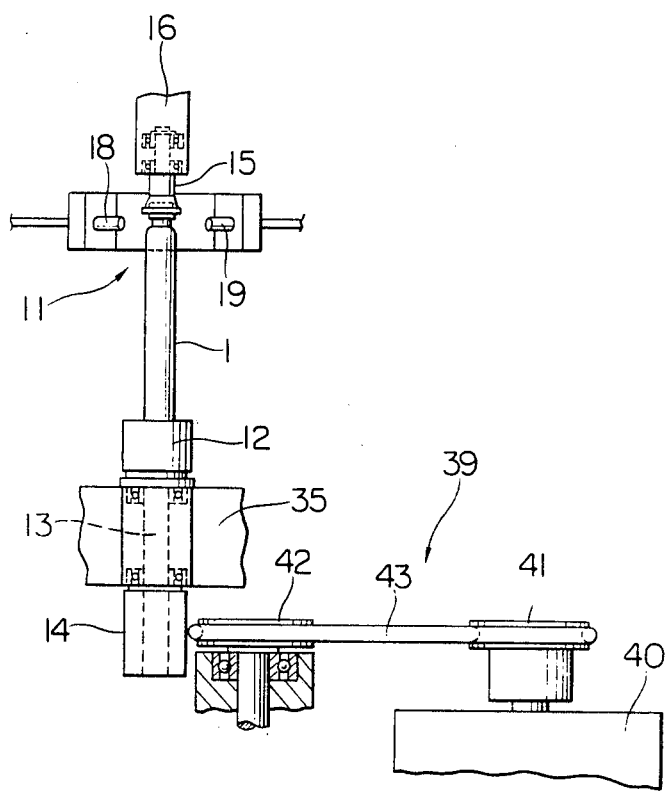
FIG. 4 is a partially cutaway enlarged front view illustrating the positional relationship between the air detecting apparatus according to this invention and a receptacle driving member in FIG. 3.

When aforesaid detecting test is carried out, the receptacle 1 is rotated at high speed by the action of belts 43 of the first driving apparatus 38 and the second driving apparatus 39. The mechanism therefore is shown in FIG. 4 together with the air detecting apparatus 11 according to this invention. Therefore, said mechanism will be explained when the detecting apparatus 11 is explained hereinafter.

Said detecting apparatus 11 will be detailed, in particular explained with reference to FIG. 4 to FIG. 6.

FIG. 4 shows the mechanism for rotating the receptacle 1 on the turntable 35 at high speed, wherein a multiplicity of rotary discs 12 are disposed, adjacent to the outer periphery of the turntable 35, at regular intervals in the circular direction, its rotary shaft 13 penetrates the table 35, is thereby supported rotatably, extends downward and is fixed at its lower end with the friction roller 14. This roller 14 is friction connected with the belt 43. Above the rotary disc 12, a rotary pad 15, which thrusts the top of the receptacle 1 downward under pressure, is attached to the table 35 through a supporting bar 16.

Figure 5:
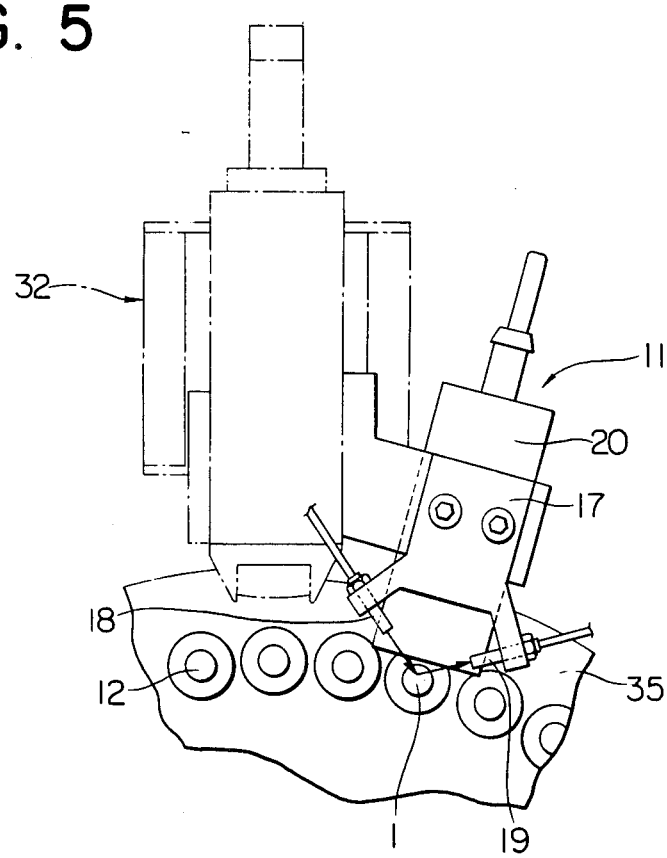
FIG. 5 is an enlarged plan view illustrating the relationship between the air detecting apparatus according to this invention and the receptacle in FIG. 3.

FIG. 5 and FIG. 6 denote the detecting apparatus 11 attached to the second detecting apparatus 32 through a bracket 17. This detecting apparatus 11 comprises a projector 18 and a ray receiver 19 which are arranged to locate below and adjacent to the seal member 4 of the receptacle 1, be at the same level and further so that when a ray projected from the projector 18 hits on the peripheral surface of the air cavity 5′ or 5″ and reflects therefrom, the reflected light may be received in the ray receiver 19.

Reference numeral 20 denotes an electrical capacitance type proximity switch. This switch 20 is designed to detect the case where the receptacle 1 is empty.

Figure 1A:
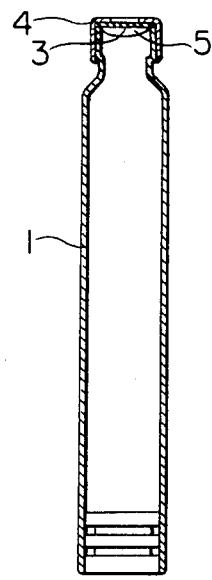
FIG. 1A is a longitudinal front elevation of a liquid receptacle whose resident air is detected by the air detecting process according to this invention.
Figure 1B:
FIG. 1B is a plan view of the receptacle of FIG. 1A.
Figure 2A:
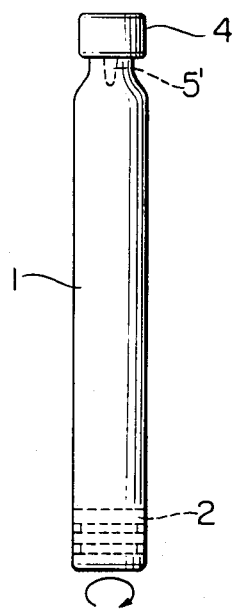
FIG. 2A is a plan view of the receptacle illustrating one mode of the resident air in the liquid receptacle to be detected by the air detecting process according to this invention.
Figure 2B:
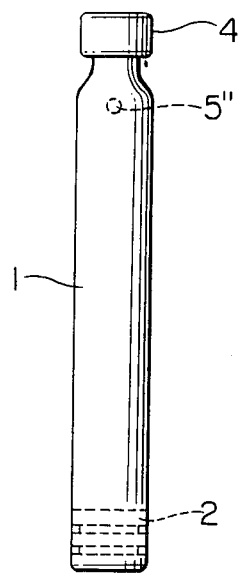
FIG. 2B is a plan view of the liquid receptacle illustrating another mode of the resident air in the same situation as FIG. 2A.

In detecting the air in the receptacle by means of the above mentioned apparatus, the receptacle 1 turning on the turntable 35 is turned at a high speed of 5,000–6,000 r.p.m. by means of the second driving apparatus 39. When a ray is projected on the thus turning receptacle 1 from the projector 18: (1) in case no air is resident in the receptacle 1, as no liquid is present at the portion of the receptacle 1 where the ray has been projected, the projected ray is not reflected and passes through and consequently the ray receiver 19 does not receive the reflected ray, (2) in case the air is resident in the receptacle 1 and its amount is relatively much, there is formed an air cavity 5′ as shown in FIG. 2A, a ray projected as shown with an arrow mark in FIG. 5 is reflected by the air cavity 5′, and the reflected ray is received by the ray receiver 19, whereby the presence of relatively much resident air can be detected. (3) in case the air is resident in the receptacle 1 but its amount is relatively small, there is no possibility that such one as the air cavity 5′ is formed during the turning motion, but as the air cavity 5″ is formed at the time stopping and descends, the projected ray is reflected from said air cavity 5″ and the reflected ray is received by the ray receiver 19. Therefore, it can be detected that the air is resident in the receptacle 1 but its amount is relatively small.

It can be seen from the aforegoing that in each case of (2) and (3) the air is detected, but the case of (3) is normally regarded as the acceptable limit because the resident air amount is small. Accordingly, the case (2) must be disposed as inferior goods, but the cases (1) and (3) dispense with such disposal.

Such being the case, if the detecting apparatus 11 is designed to send its detection signal to a selecting member 46 only in the case of (2), it becomes possible to select only the receptacles 1 under the conditions as shown in FIG. 2A as inferior goods and carry them on the conveyor for discharge. In the aforesaid embodiment, the air detecting apparatus 11 is placed side by side with the second detecting apparatus 32, but should not limited thereto, that is may be placed side by side with the first detecting apparatus 31. And, it is needless to say that said detecting apparatus 11 may be used singly entirely having no connection with these detecting apparatuses.

Although a particular preferred embodiment of the invention has been disclosed in detail for illustrative purposes, it will be recognized that variations or modifications of the disclosed apparatus, including the rearrangement of parts, lie within the scope of the present invention.

What is claimed is:

1. A process for detecting resident air with a liquid-containing receptacle, said receptacle comprising:
    a transparent liquid container having a first axis, a first end and a second end, said first and second ends spaced apart along said first axis, said first end being open, and
    an opaque sealing member disposed over said first end and extending a first predetermined axial distance from said first end over said liquid container adjacent said first end, said opaque sealing member fluid-tightly sealing said first end, said extension of said sealing member over said liquid container defining a first volume in said liquid container, said first volume being sufficient to contain a second volume of air, said second volume being less than said first volume, when said first axis is vertically aligned and said first end is uppermost, such that upon rotation of said receptacle about said first axis at a predetermined speed a light-reflective air-liquid interface will form between said second volume of air and said liquid which will extend a second predetermined axial distance from said first end further than said first predetermined axial distance,
    said process comrpising:
    supporting said receptacle with said first axis vertically aligned and said first end uppermost;
    providing a light beam projector having an optical axis;
    providing a light detector having an optical axis;
    disposing said light beam projector and said light detector so that their optical axes lie in a common plane, said common plane being substantially transverse to said first axis and intersecting said liquid container at said second predetermined axial distance from said first end, said optical axes forming an angle in said common plane such that light projecting from said light beam projector is reflectable from an air-liquid interface in said liquid container to said light detector;
    rotating said receptacle about said first axis at said predetermined speed;
    projecting a light beam from said light beam projector to said receptacle; and
    determining whether reflected light is detected by said light detector.

2. The process according to claim 1, further comprising the step of abruptly stopping rotation of said receptacle about said first axis.

3. The process according to claim 1, wherein said predetermined speed is 5,000–6,000 RPM.

4. An apparatus for detecting resident air within a liquid-containing receptacle, said receptacle comprising:
    a transparent liquid container having a first axis, a first end and a second end, said first and second ends spaced apart along said first axis, said first end being open, and
    an opaque sealing member disposed over said first end and extending a first predetermined axial distance from said first end over said liquid container adjacent said first end, said opaque sealing member fluid-tightly sealing said first end, said extension of said sealing member over said liquid container defining a first volume in said liquid container, said first volume being sufficient to contain a second volume of air, said second volume being less than said first volume, when said first axis is vertically aligned and said first end is uppermost, such that upon rotation of said receptacle about said first axis at a predetermined speed a light-reflective air-liquid interface will form between said second volume of air and said liquid which will extend a second predetermined axial distance from said first end further than said first predetermined axial distance,
    said apparatus comprising:
    receptacle holding means, having a vertical axis, for holding said receptacle with said first axis coaxially aligned with said vertical axis and said first end uppermost, said receptacle holding means being rotatable about said vertical axis;
    supporting means for supporting said receptacle holding means for rotation about said vertical axis;
    driving means for rotating said receptacle holding means about said vertical axis at said predetermined speed; and
    optical detecting means for detecting said light-reflective air liquid interface, said optical detecting means comprising a light beam projector having an optical axis and a light detector having an optical axis, said light beam projector and said light detector disposed so that their optical axes lie in a common plane, said common plane being substantially transverse to said vertical axis and intersecting said receptacle at said second predetermined axial distance from said first end, said optical axes forming an angle in said common plane such that light projecting from said light beam projector is reflectable from said air-liquid interface in said receptacle to said light detector.

5. The apparatus according to claim 4, wherein said receptacle holding means comprises a rotary pad, having an axis, which presses downwardly against a top portion fo said receptacle, a rotary disc, having an axis, which is disposed beneath said rotary pad and supports a bottom portion of said receptacle, and a friction roller, having an axis, which is disposed coaxially with said rotary pad and is coaxially connected with said rotary disc; said driving means comprises a rotatable belt which is frictionally contactable with said friction roller and a motor, operably connected to said belt, for rotating said belt.

6. The apparatus according to claim 4, wherein said predetermined speed is 5,000–6,000 RPM.

* * * * *